United States Patent [19]
Dudley

[11] Patent Number: 5,524,495
[45] Date of Patent: Jun. 11, 1996

[54] LIQUID SAMPLING DEVICES AND METHOD

[75] Inventor: Lynn A. Dudley, Chino, Calif.

[73] Assignee: Vortox Company, Claremont, Calif.

[21] Appl. No.: 421,474

[22] Filed: Apr. 12, 1995

Related U.S. Application Data

[63] Continuation of Ser. No. 75,215, Jun. 9, 1993, abandoned, which is a continuation-in-part of Ser. No. 902,067, Jun. 22, 1992, abandoned.

[51] Int. Cl.$^6$ ........................................... G01N 1/20
[52] U.S. Cl. ........................... 73/863.52; 73/863.57; 73/864.63
[58] Field of Search ..................... 73/863.52, 863.43, 73/863.57, 864.63, 864.51, 170.17–170.23

[56] References Cited

U.S. PATENT DOCUMENTS

| | | | |
|---|---|---|---|
| 3,929,003 | 12/1975 | Llewellyn | 73/61.72 |
| 4,762,009 | 8/1988 | Scrudato | 73/863.52 |
| 4,958,528 | 9/1990 | Garrison | 73/864.63 |
| 5,069,878 | 12/1991 | Ehrenkranz | 73/863.52 X |
| 5,186,052 | 2/1993 | Gray | 73/215 |
| 5,220,825 | 6/1993 | Peterson | 73/863.01 |
| 5,279,151 | 1/1994 | Coody et al. | 73/863.52 |
| 5,347,877 | 9/1994 | Gadbois | 73/863.52 |
| 5,408,892 | 4/1995 | Kawanami et al. | 73/170.17 X |

OTHER PUBLICATIONS

*Water Resources Research*, vol. 16, No. 3, pp. 592–596, Jun. 1980 "Development of a Self-Sealing Rain Sampler for Acid Zones"; E. Adar et al.

*Primary Examiner*—Thomas P. Noland
*Attorney, Agent, or Firm*—Boniard I. Brown

[57] ABSTRACT

Liquid sampling devices and methods for sampling flowing or other liquid to determine its composition. The preferred sampling device has an upper liquid catch basin 40 for receiving a liquid to be sampled, a lower sample collection chamber 20, a liquid inlet 24 communicating the basin and collection chamber, and an inlet valve 26, 28 for closing the inlet against entry of liquid and foreign matter into the chamber and escape of liquid and vapor from the chamber except when the inlet is submerged in liquid to be sampled and the collection chamber contains less than a predetermined volume of the liquid. The sampling device is placed in sampling position such that the inlet valve 26, 28 remains closed until liquid covers the inlet 24, whereupon the inlet valve opens to permit liquid flow into the collection chamber 20 and later recloses in response to filling of the chamber with a predetermined sample volume. Exemplary uses of the sampling device are sampling storm water runoff from industrial property to determine the contaminants, if any, absorbed by the storm water as it flows across the property, and sampling liquid leakage in a brewery or other liquid processing facility to aid in locating the leak.

51 Claims, 4 Drawing Sheets

LIQUID SAMPLING DEVICES AND METHOD

RELATED APPLICATION

This is a continuation of application Ser. No. 08/075,215 filed on Jun. 9, 1993, and now abandoned. Ser. No. 08/075,215 was a continuation-in-part of my application Ser. No. 07/902,067, filed Jun. 22, 1992, entitled "Storm Water Runoff Sampler", and now abandoned.

BACKGROUND OF THE INVENTION

1. Field of the Invention

This invention relates generally to the art of sampling a liquid for the purpose of analyzing the liquid to determine its composition. The invention relates more particularly to novel liquid sampling methods and devices for this purpose.

2. Prior Art

It will become readily evident as the description proceeds that the liquid sampling methods and devices of this invention may be utilized for a variety of liquid sampling purposes and to sample a variety of liquids in a variety of sampling environments. One sampling application of the invention which is of particular importance at the present time involves sampling storm water runoff from industrial property to determine the presence of toxics and other contaminants, if any, in the runoff. Another useful application involves sampling liquid leakage from industrial liquid processing equipment to aid in locating the leak(s). The invention will be described in the context of these particular applications. Other possible uses of the invention will be mentioned and involve sampling liquid in a storm drain system or other liquid conductor, sampling liquid discharge from a sewage treatment plant or an industrial process or the like, and sampling liquid in a body of liquid. The invention may be utilized to sample liquids from any type of fluid conductor including surfaces, open channels, or closed pipes or ducts, and liquids which are either homogenous liquids, mixtures of miscible liquid components, or mixtures of immiscible liquid components.

The water flowing through public storm drain systems often contains toxic and other contaminants which end up polluting large public water bodies, such as the San Diego, Santa Monica, and San Francisco Bays in California. Much of this contamination is due to deliberate and illegal dumping of industrial waste products into the storm drain systems in order to avoid the problems and cost associated with legal disposition of such waste products. The liquid sampling methods and devices of this invention may be utilized to sample the water flowing through these storm drain systems for the purpose of determining the presence and source of such contaminants.

Another extensive source of contamination of the water in storm drain systems is storm water runoff from industrial property and the like. Thus, the ground and other exterior surfaces of such property are often covered by or contain a relatively high concentration of various industrial substances due to spillage of the substances onto the surfaces and the ground, leakage of the substances into the soil from pipes or storage containers, and hosing of the substances from interior floor areas onto exterior surface areas and the ground. During a rainstorm, these substances are entrained in the storm water runoff from the property and are carried with the storm water runoff into the public storm drain system.

In an effort to reduce such storm water runoff pollution, the state of California recently passed legislation establishing a program entitled the Industrial Storm Water Permitting Program. This program requires industrial property owners to obtain a permit, referred to as a General Industrial Storm Water Permit, for storm water runoff or discharge from their properties into the public storm drain system. The permits are issued through the State Water Resources Control Board.

Obtaining such a permit involves the payment of an annual fee and the performance by each applicant, referred to as a discharger, of certain obligations. These obligations include the following: (a) preparation of a site map of the property in question, starting with the roof each building on the property, showing the flow path of storm water runoff from the roof to the ground, then across the ground into the drain system on the property, and then from the property drain system into the public storm drain system; (b) visual observation of storm water discharge from the property during both the wet season (October through April) and the dry season (May through September); (c) submission of an estimate or calculation of the storm water discharge volume during two significant storm events in the wet season; (d) submission, for approval, of a proposed storm water sampling program; (e) execution of the approved storm water sampling program in compliance with the state regulations to obtain certain storm water samples; and (f) submission of the storm water samples for analysis.

Requirement (e) above of the Industrial Storm Water Permitting Program dictates that storm water samples be obtained during two separate storm events of the wet season and that one of these events be the first storm event of the wet season which produces significant storm water runoff preceded by at least 72 hours of dry weather. The storm water samples collected during each storm event must include a "grab sample" and a "composite". A grab sample in a storm water sample taken during the first thirty minutes of the discharge (or within the first hour of the discharge with explanation). A composite sample may be a sample taken with a continuous sampler or the combination of at least three grab samples taken during each hour of discharge with the successive grab samples being separated by a minimum period of at least 15 minutes. A composite sample shall be either flow-weighted (i.e. consist of a mixture of aliquots collected at constant time intervals, where the volume of each aliquot is proportional to the flow rate of the discharge) or time-weighted (i.e. consist of a mixture of equal volume aliquots collected at constant time intervals). Grab samples are used for determining certain specific contamination levels. Composite samples are used to obtain an estimate of average runoff water quality.

From the above discussion, it is evident that storm water sampling in compliance with the above-stated requirements of the Industrial Storm Water Permitting Program presents two basic problems. These problems are (a) having a storm water sampler in proper sampling readiness and position at the start of the first significant storm event of a wet season to collect a sample of the storm water runoff during the first 30 minutes of the discharge which will qualify as a valid "grab sample", and (b) having a storm water sampler in proper sampling readiness and position at the start of the first storm event of a wet season to collect a sample or samples of the storm water discharge during the first 3 hours of the discharge which will qualify as a valid "composite sample".

One way in which such valid grab and composite samples may be assured, of course, is to have persons standing by 24 hours a day during each and every day preceding the wet season in constant readiness to place storm water samplers in proper sampling positions immediately upon the start of each storm event to be monitored.

Obviously, this is an impractical solution to the storm water sampling problem. Moreover, there are numerous other situations in which liquid sampling is desirable or essential and which involve essentially the same or other similar sampling problems and requirements as storm water runoff sampling. Accordingly, there is a definite need for liquid sampling methods and devices for these and other liquid sampling purposes.

SUMMARY OF THE INVENTION

This invention provides novel liquid sampling methods and devices which satisfy the requirements of the Industrial Storm Water Permitting Program and yield storm water grab samples and time composite samples that comply with such requirements. Accordingly, the sampling methods and devices are ideally adapted for storm water sampling. In this regard, for example, the sampling devices may be placed in sampling position well before the onset of the wet season where they remain in total readiness, without human attention, to collect a storm water grab sample and/or a storm water time composition sample within the prescribed times during the first storm vent of the wet season or during a later storm event to be monitored.

While ideally adapted for storm water sampling, the liquid sampling methods and devices of the invention are uniquely capable of many other diverse liquid sampling uses, some of which will be discussed or mentioned later. According to its broader aspects, therefore, the invention provides liquid sampling methods and devices for collecting samples of any liquid for any purpose. The liquid sampled may be a homogeneous liquid, a mixture of immiscible liquid, or a mixture of miscible liquids.

Simply states, a liquid sampling device according to the invention, referred to in places simply as a liquid sampler, comprises a receptacle having a normally lower sample collection chamber, normally upper inlet means having an inlet passage through which liquid to be sampled can enter the chamber, and a drain valve through which a collected sample can be drained from the chamber. In use, the sampler is placed in a sampling position where in the inlet passage is disposed to receive the liquid to be sampled.

The described sampling devices of the invention are intended for storm water sampling, leak sampling, and other similar sampling uses and have an upper catch basin into which the inlet passage opens. For storm water sampling, the sampler is placed in sampling position within a sump or the like located in the anticipated flow path of storm water runoff from the property to be monitored. At least some of the storm water flowing into the sump enters the sampler basin and then flows from the basin through the sampler inlet passage into the sampler collection chamber. For leakage sampling, the sampler is similarly placed in sampling position in a sump in the floor along which the leakage liquid flows. In other liquid sampling applications, a sampling device according to the invention may be positioned to sample liquid effluent from or flow through a pipe, channel, or other fluid conductor or immersed in a body of the liquid to be sampled. After the desired sample has been collected, the sampler is removed to a laboratory where the collected sample is drained from the sampler and analyzed.

According to one important feature of the invention, the inlet means of the sampling device includes inlet valve means for opening and closing the inlet passage to the collection chamber. This inlet valve means has a standby mode in which the valve means close the inlet passage against entry of foreign matter into the collection chamber, a sampling mode in which the inlet valve means open the inlet passage for entry of the liquid being sampled into the collection chamber, and a sample containment mode in which the inlet valve means close the inlet passage against liquid entry into and escape of liquid and vapor from the collection chamber. The inlet valve means assumes its standby mode in the absence of liquid covering the upper inlet end of the inlet passage. The inlet valve means assumes its sampling mode when the inlet end of the inlet passage is covered with liquid and the collection chamber contains less than a predetermined volume of liquid, that is when the liquid level in the collection chamber is below a predetermined level. The inlet valve means assumes its sample containment mode when the collection chamber contains at least the predetermined volume of liquid, that is when the liquid level in the collection chamber at least equals the predetermined level.

In the described embodiments of the invention, the inlet valve means comprise an upper float valve engagable with an upper valve seat about the upper end of the inlet passage and a lower float valve engagable with a valve seat about the lower end of the inlet passage. The upper float valve is movable between a lower closed position wherein the upper valve engages the upper valve seat to close the upper end of the inlet passage and an upper open position wherein the upper float valve is spaced upwardly from the upper valve seat to open the upper end of the inlet passage. The lower float valve is movable between an upper closed position wherein the lower valve engages the lower valve seat to close the lower end of the inlet passage, and a lower open position wherein the lower float valve is spaced downwardly from the lower valve seat to close the lower end of the inlet passage.

When the sampling device occupies its normal upright position with the upper catch basin and lower collection chamber empty, the lower float valve remains in its lower open position and thereby opens the lower end of the inlet passage. The upper float valve, on the other hand, remains in its lower closed position and seals the upper end of the inlet passage against entrance of foreign matter into the collection chamber during storage and handling of the device and prior to the basin receiving liquid to be sampled after placement of the device in sampling position.

When the liquid level in the basin rises to the height of the upper end of the inlet passage, the liquid lifts the upper float valve off its valve seat and enters the collection chamber through the inlet passage. If liquid inflow into the basin continues, the collection chamber will eventually fill with the liquid to a level sufficient to elevate the lower float valve to its closed position and thereby seal the lower end of the inlet passage even though the upper float valve remains open. This closure of the lower float valve occurs in response to accumulation of a liquid sample of predetermined volume in the collection chamber, and prevents subsequent dilution of the collected sample by continued liquid flow into the sampler basin or by deliberate action of a person seeking to falsify the sample. Closure of the lower valve also prevents escape of liquid vapor from the collection chamber.

The disclosed liquid sampling devices of the invention have provision for flushing and cleaning the collection chamber after each use to avoid contamination of later collected liquid samples by residue from earlier collected samples. In one disclosed embodiment, the inlet means is positioned within an opening in an upper and wall of the collection chamber and is removable to provide cleaning access to the chamber through this opening. In another disclosed embodiment, the upper end wall of the collection chamber is a cover which mounts the inlet means and is removable to provide a large opening through which the chamber may be flushed and cleaned with ease.

According to a preferred feature of the invention, certain disclosed embodiments of the invention are provided with means for adjusting the maximum inflow rate of the liquid being sampled into the collection chamber and thereby adjust the maximum sampling duration of the of the sampling device. In these embodiments, the adjustment means is a limit stop for the upper float valve which is adjustable to vary the maximum opening separation of the upper valve from its valve seat.

One disclosed embodiment of the invention has an inlet riser through which liquid enters the collection chamber and which rises above the floor of the sampler basin. This riser delays entry of liquid into the collection chamber until the liquid level in the basin rises to the level of the upper end of the riser and is useful for storm water sampling applications. Another disclosed embodiment is time composite sampling device, that is a sampling device for collecting separate consecutive samples of a liquid over a period of time. This sampling device comprises a plurality of separate sample collection chambers and an inlet means for each chamber. These separate inlet means are arranged so that the liquid being sampled fills one collection chamber first, then the next collection chamber, and so on in such a way that the chambers are filled successively at spaced intervals. The preferred composite sampling device of the invention comprises at least two separate collection chambers having inlet risers of different height above the floors of their catch basin(s).

DESCRIPTION OF THE PREFERRED EMBODIMENTS

Figures 1, 2, 3:
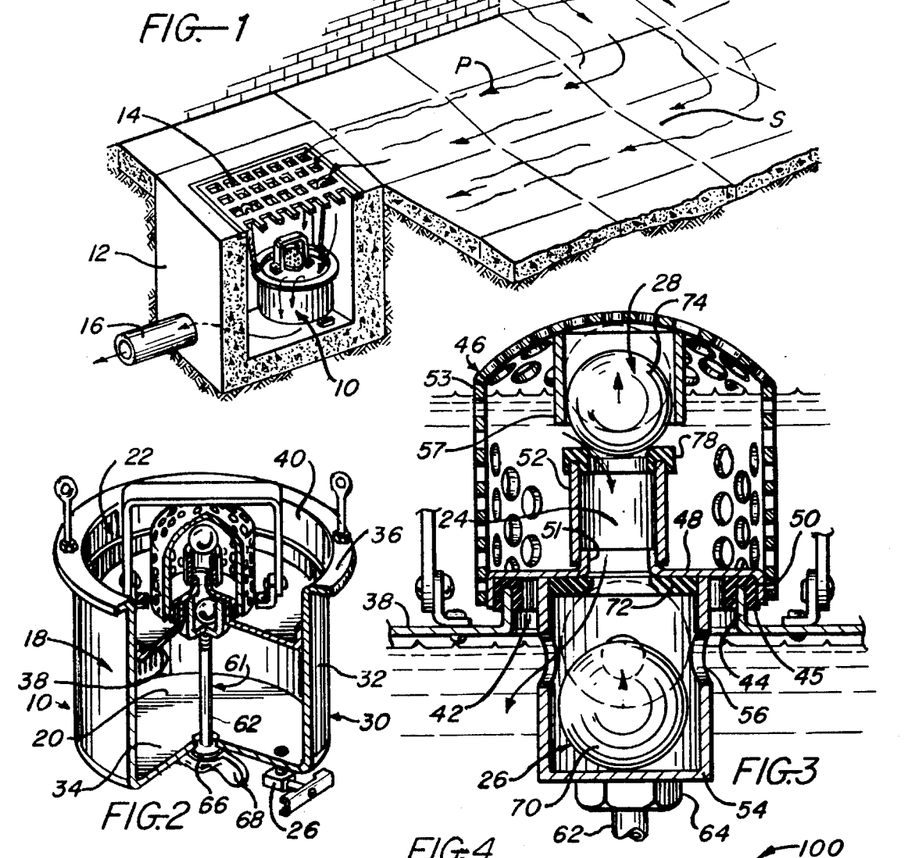
FIG. 1 is a perspective view of a liquid sampling device according to this invention located in sampling position.
FIG. 2 is an enlarged perspective view, partly in section, of the sampling device in FIG. 1.
FIG. 3 is an enlarged partial vertical sectional view of the storm water sampler of FIG. 2, illustrating ball valves embodied in the sampler for sealing the sampler collection chamber against dilution of the collected storm water sample, against entry of foreign objects into the sample collection chamber during periods of non-use, and against escape of volatile elements in the sample.

Turning now to these drawings and first to FIGS. 1–3, there is illustrated a liquid sampling device 10 located in sampling position in the path of a moving liquid S. As mentioned earlier and will be explained in more detail later, a sampling device according to the invention may be utilized to sample a greater variety of liquids, including homogeneous liquids and liquid mixtures composed of either miscible or immiscible liquid components, in a variety of sampling environments and for a variety of purposes. Also, the sampling device may be disposed in sampling relation to the sampled liquid in various ways including placement of the device in the path of a moving liquid, as in FIGS. 1–3, and submersion of the device in a body of liquid.

A particularly useful and important application of the sampling device involves sampling storm water runoff from an industrial property in accordance with the Storm Water Permitting Program referred to earlier. For convenience, the illustrated sampling device 10 is described primarily in the context of this particular use in which the sampled liquid is the storm water runoff.

The illustrated storm water sampler 10 is placed in sampling position within a concrete sump 12 located in the path P of the storm water runoff from the industrial property to be monitored. The sump has an open top covered by a removable grate 14. The sump is located in the storm water flow path P with the grate 14 substantially flush with the surrounding surface along which the storm water flow occurs. A subterranean drain line 16 leads from the bottom of the sump.

The storm water sampler 10 comprises a receptacle 18 having a normally lower sample collection chamber 20 and normally upper inlet means 22. This inlet means includes an inlet passage 24 through which storm water can enter the collection chamber. The sampler is positioned in the sump 12 in such a way that sampler inlet means 22 receives storm water entering the sump through the grate 14. At least some of the storm water flows through the inlet passage 24 into the collection chamber 20 until the chamber is filled to a predetermined level, which is the level of FIG. 3. The contents of the chamber then constitutes a storm water sample which can be drained from the chamber through a drain valve 26 at the bottom of the collection chamber and analyzed to determine the presence of contaminants, if any, in the sample picked up by the storm water as it flowed across the industrial property in question.

In order to assure an accurate storm water sample which complies fully with the Storm Water Permitting Program, it is necessary to prevent dilution and contamination of a collected storm water sample by entry of foreign matter into the collection chamber prior to actual storm water sampling during a storm event, by continued storm water flow over the sampling device following collection of a complete storm water sample, and by deliberate action of a person seeking to alter the collected sample. To prevent such dilution and contamination, the sampler inlet means 22 includes inlet valve means 26, 28 which close the inlet passage 24 except when both of the following conditions exist: (a) the upper inlet end of the inlet passage is covered by the liquid to be sampled, and (b) the collection chamber 20 contains less than a predetermined volume of the liquid. This predetermined volume of liquid constitutes a complete storm water sample and occurs when the collection chamber contains storm water to a predetermined level (the level of FIG. 3). The valve means 26, 28 also block escape from the collection chamber of the collected sample liquid and volatile elements present in, that is vapor from, the collected sample. The terms "upper end" and "lower end" as applied herein to the collection chamber are used in a broad sense to means the top and bottom of the chamber in tits normal sampling position regardless of the physical shape of the chamber.

Referring now in more detail to FIGS. 1–3, the sampler receptacle 18 comprises a generally cup-shaped body 30 having a cylindrical side wall 32, a bottom wall 34, and an outwardly directed flange or rim 36 about the open, normally upper end of the body. Extending across the interior of the body 30 between its bottom wall 34 and rim 36 is an annular partition wall 38 which is welded or otherwise permanently secured and sealed to the side wall 32. The space between this partition wall and the bottom wall 34 forms the storm water sample collection chamber 20.

The partition wall 38 and the upper end portion of the side wall 32 which extends above the partition wall form a normally upper and upwardly opening storm water catch basin 40 at the upper end of the receptacle 18. The partition wall forms the floor of this basin. The portion of the side wall 32 above this floor forms the side wall of the basin which terminates at its upper end in the rim 36. At the center of the partition wall or basin floor 38 is a circular opening 42 circumferentially surrounded by an upstanding flange 44. Positioned over the upper edge of this flange 44 is resilient seal ring 45 having a coaxial circular slot in its lower edge receiving the flange.

Inlet means 22 comprises an inlet fitting 46 removably and coaxially positioned within the basin floor opening 42. This inlet fitting includes, between its ends, an annular plate 48 whose outer edge portion is turned downwardly to form a depending cylindrical flange 50 about the plate. The inner diameter of this flange is sized to fit closely but removably over the seal ring 45. The inner edge portion of the plate 48 is turned upwardly to form an upstanding cylindrical flange 51 about the central opening in the plate. Rigidly joined to and extending coaxially upwardly from the flange 51 is a tubular inlet riser 52 which projects a distance upwardly above the basin floor 38.

A strainer 53 of inverted cup shape is positioned over the riser 52. The open bottom of this strainer fits over and is secured to the depending flange 50 on the fitting plate 48. Rigidly joined to and coaxially depending of the underside of the plate is a lower cup-shaped valve cage 54 having ports 56 in its side wall. Fixed to the inside of the strainer 53 over and coaxial with the inlet riser 52 is an upper valve cage 57 of inverted cup shape.

The inlet fitting 46 is removably positioned on the partition wall or basin floor 38 with the fitting plate 48 above and seating downwardly against the seal ring 45 and with the plate flange 50 circumferentially surrounding the seal ring. The lower fitting valve cage 54 depends coaxially through the basin floor opening 42 into the collection chamber 20. The inlet fitting is releasably secured in position by connecting means 61 including a shaft 62. Shaft 62 extends upwardly and coaxially through the bottom wall 34 of the collection chamber 20 and is threaded at its upper end in a nut 64 rigidly joined to the bottom wall of the lower valve cage 54. Threaded on the lower end of the shaft, below the bottom wall 34 of the collection chamber 20, are a seal ring 66 and a wing-nut-like grip 68. The shaft is fixed against rotation relative to either the nut 64 or the grip 68, whereby the grip is rotatable to firmly clamp the inlet fitting plate 38 against the seal ring 45 and thereby secure and seal the fitting to the catch basin floor 38 about the floor opening 42.

The inlet passage 24 extends longitudinally through and opens through the upper end of the inlet riser 52. The upper end of the riser is located at a level between the upper rim 36 and floor 38 of the basin 40. The lower end of the inlet passage 24 opens to the collection chamber 20 through the valve lower cage 54 and its side wall ports 56.

The lower inlet valve means 26 of the storm water sampler comprise a buoyant ball forming a float valve 70 within the lower valve cage 54. This float valve is engagable with a downwardly facing annular valve seat 72 about the lower end of the inlet passage 24. The upper inlet valve means 28 comprises a buoyant valve ball forming a float valve within the upper valve cage 57. This upper float valve is engagable with an upwardly facing annular valve seat 78 about the upper end of the inlet riser 52.

The storm water sampling device 10 is used in this fashion. Prior to the first storm event of the wet season, the sampler is hung in storm water sampling position within the sump 12 located in an anticipated storm water runoff flow path from the industrial property to be monitored, as shown in FIG. 1. Prior to the first storm event, the upper float valve 74 will engage its seat 78 to close the inlet passage 24 against entry of dirt, rocks and other foreign matter into the collection chamber 20.

During the first storm event, storm water runoff from the property flows into the sump 12 and enters sampler catch basin 40. When the water level in the basin reaches the upper end of the inlet riser 52, the water raises the upper float valve 74 from tis valve seat 78 to an open position within the upper valve cage 76. Storm water then flows from the basin, through the inlet passage 24 into the sampler collection chamber 20. This chamber may have a volume on the order of one gallon. Assuming sufficient rainfall, the collection chamber will eventually fill sufficiently to provide a "grab sample" of the first storm water runoff from the property. As the chamber fills, the lower float valve 70 is raised from its solid line open position of FIG. 3 to its broken line closed position of engagement with its valve seat 72 to close the inlet passage 24. This closure of the lower float valve occurs when the water in the collection chamber 20 reaches a predetermined level (the level shown in FIG. 3) at which the chamber contains a storm water sample of predetermined volume. Closure of the lower float valve prevents dilution and contamination of the collected sample by continuing storm water flow over the sampler or by deliberate action of a person seeking to alter the sample. Closure of the lower float valve also prevents escape of storm water and vapor from the collection chamber. The inlet riser 52 delays flow of storm water from the basin into the collection chamber and acts as a dam which prevents passage of sand, dirt, silt or the like into the collection chamber.

When the storm ends or the sampling device is removed from the sump 12, the upper valve ball 74 will reengage its valve seat 78 to seal the upper end of the inlet passage 24 against entry of foreign mater. The sampling device is carried to a laboratory by its illustrated handle, where the collected sample is drained for the collection chamber 20 through the lower drain valve 26 for analysis. The inlet fitting 46 is then removed for the receptacle 18 to permit thorough flushing and cleaning of the fitting and the collection chamber through the basin floor opening 42 to avoid contamination of later collected samples.

From the above description, it is evident that the inlet valve means 26, 28 have, in effect, a standby mode in which the upper float valve 74 is closed and the lower float valve 70 is open, a sampling mode in which both float valves are open, and a sample containment mode in which the lower float valve or both float valves is/are closed. The valve means assume the standby mode during storage of the sampling device and when the sampling device is in sampling position awaiting the liquid to be sampled. The valve means assume the sampling mode when the upper inlet end of inlet passage is covered with liquid and the collection chamber contains less than the predetermined volume of liquid necessary to constitute a complete liquid sample. The valve means assume the sample containment mode when the collection chamber contains a complete liquid sample and the upper float valve is either open or closed.

Figure 4:
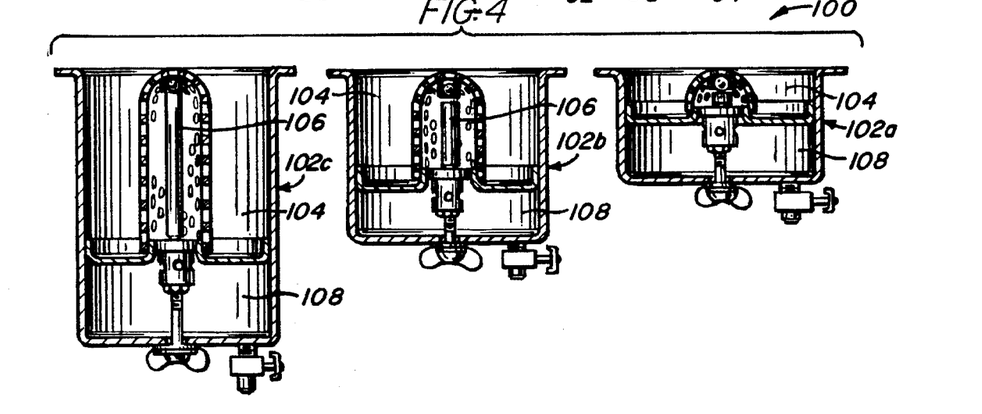
FIG. 4 is a cross-section through a modified liquid sampling device according to the invention for collecting a time composite liquid samples.

FIG. 4 illustrates a modified storm water sampling device 100 according to the invention for collecting, at spaced intervals, three separate storm water samples which, together, constitute a time composite storm water sample. This composite sampling device comprises, in effect, three separate storm water samplers 102a, 102b, 102c, each essentially identical, except for dimensions, to the storm water sampler of FIGS. 1–3. Accordingly, it is unnecessary to describe each individual composite sampler in elaborate detail. Suffice it to say that the three samplers 102a, 102b, 102c differ from one another and from the sampler in FIGS. 1–3 only in the depth of their upper storm water receiving basins 104 and the height of their inlet risers 106. Thus, the basin depths and riser heights of the three samplers increase progressively. The dimensions and volumes of the sampler collection chambers 108 are equal to one another and to that of FIGS. 1–3. The individual composite samplers are otherwise identical to that of FIGS. 1–3.

In use, the storm water time composite sampling device of FIG. 4, is placed in sampling position within an anticipated storm water runoff flow path from an industrial property to be monitored in the same way as described in connection with FIGS. 1–3 so that the storm water enters the upper storm water catch basins 104 of the device. Because of the different basin depths and riser heights of the sampling device, a first storm water sample will be collected in the collection chamber 108 of the sampler 102a with the shallowest basin and lowest riser height. After a period of time determined by the differing basin depths and riser heights, a second storm water sample will be collected in the collection chamber 108 of sampler 102b. After another period of time, a third storm water sample will be collected in the collection chamber of sampler 102c. By properly sizing the individual samplers 102a, 102b, 102c, the time composite sampling device of FIG. 4 may be designed to collect three equal storm water samples at three spaced intervals during a storm event.

As mentioned earlier, storm water sampling is but one of the many possible uses to the liquid sampling device of the invention. Another possible use involves sampling of liquid leaking from industrial equipment to aid in locating the source of the leak(s). In this regard, assume that FIG. 1 illustrates the floor of a large industrial facility, such as a brewery, having liquid handling equipment at many locations about the facility and that the liquid S on the floor is from a leak or leaks in this equipment which cannot be located by direct inspection. Assume further that the processes performed in the equipment are such that the composition of the leakage liquid will be determined, at least to some extent, by the location of the leak(s) in the equipment. Accordingly, analysis of the leakage liquid will aid in locating the source of the leak(s).

The liquid sampling device of this invention may be used to collect samples of the leakage liquid for analysis and thereby aid in locating the leaks. In FIG. 1, for example, the liquid sampling device 10 of the invention may be placed in sampling position within a sump 12 in the floor of the facility to sample leakage liquid S flowing along the floor. Sampling operation of sampling device in this application, of course, is exactly the same as described earlier in connection with storm water sampling. Other uses of the sampling device are also possible. In some cases, a liquid sample might be collected by submerging the sampling device in a body of the liquid. In other cases, the sampling device might be located to sample liquid flowing through a pipe or other fluid conductor or to sample liquid effluent from such a liquid conductor.

Figure 5:
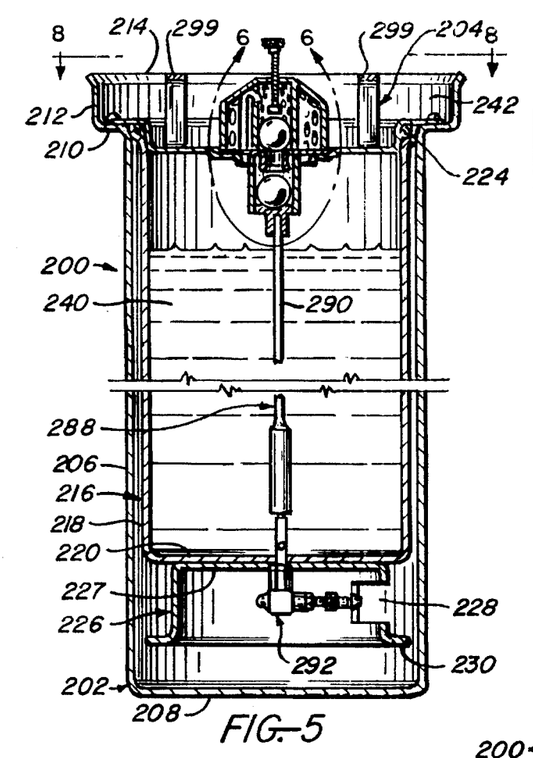
FIG. 5 is a longitudinal section through a further modified liquid sampling device according to the invention.
Figure 6:
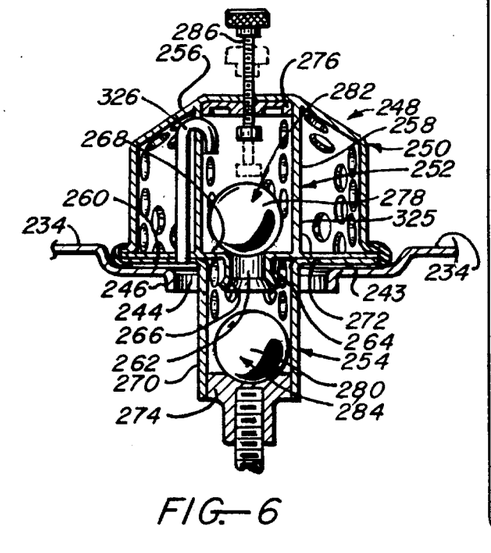
FIG. 6 is an enlargement of the area encircled by the arrow 6—6 in FIG. 5.
Figure 7:
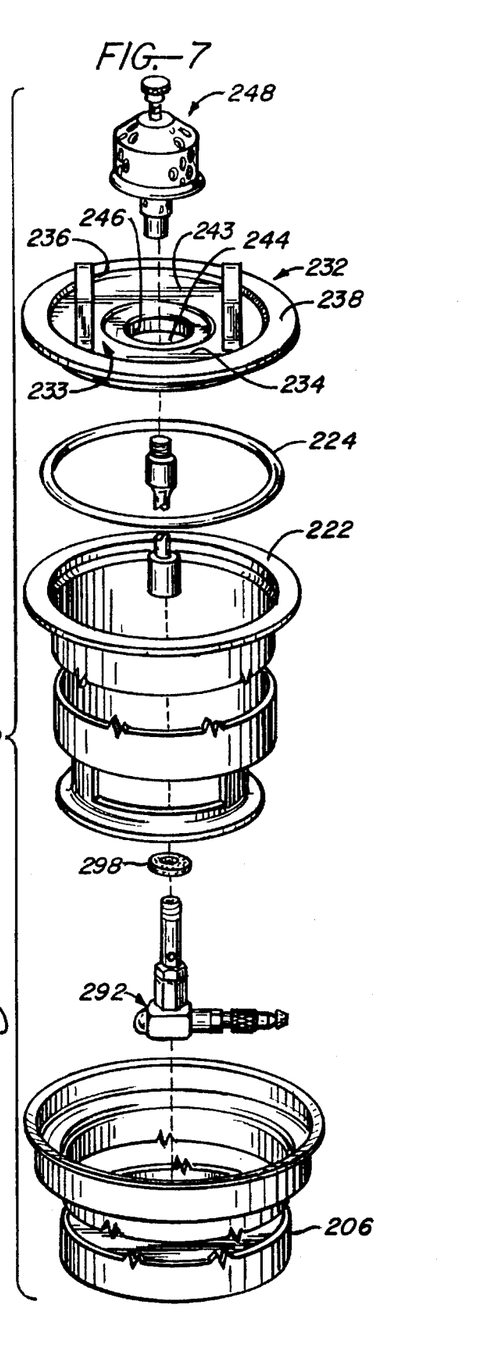
FIG. 7 is an exploded perspective view of the sampling device in FIG. 5.
Figure 8:
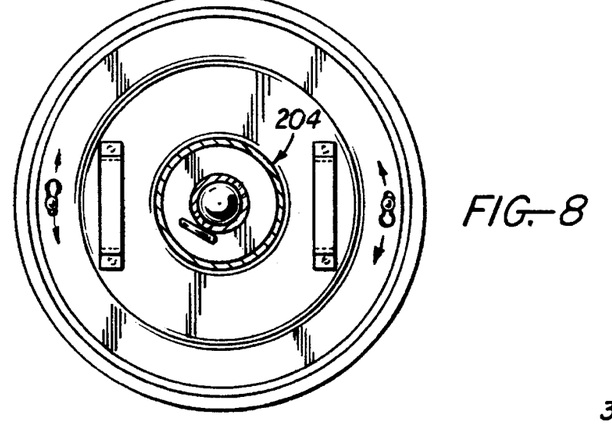
FIG. 8 is a view looking in the direction of the arrows on the line 8—8 in FIG. 5.

Referring now to FIGS. 5–7, the illustrated liquid sampling device 200 comprises an outer casing 202 having an open upper end, and a liquid sampler 204 proper positioned in casing 202 and removable from the casing through its upper end. The casing 202 has a cylindrical side wall 206, a bottom wall 208, and an annular shoulder 210 extending circumferentially about the upper end of the side wall and terminating along its radially outer edge in an upstanding cylindrical wall portion 212. The upper edge of this wall portion turns outwardly to form a lip or rim 214.

The liquid sampler 204 is very similar in construction and operation to the sampler of FIGS. 1–3. The sampler 204 includes a generally cup-shaped cylindrical receptacle 216 having an open upper end, a cylindrical side wall 218, and a bottom wall 220. The upper end portion of the side wall 218 turns outwardly to form an annular flange 222 and an upwardly opening annular seat for an O-ring seal 224 circumferentially surrounding the open upper end of the receptacle. Coaxially disposed below the bottom wall 22 of the receptacle 216 is a base 226 of inverted cup-shape for supporting the sampler 204 when it is removed from the casing 202. The base has a top wall 227 seating against and rigidly joined to the bottom wall 220 of the sampler receptacle 216, a sidewall opening 228 whose purpose will be explained presently, and a lower flange 230.

The sampler 204 is sized in diameter and length to fit closely but removably within the casing 202 with the sampler flange 222 seating on the casing shoulder 210 to vertically support the sampler in the casing. In this supported position, the bottom flange 228 of the sampler base 226 is spaced from the bottom wall 298 of the casing, as shown in FIG. 5. When the sampler is removed from the casing, the base is used to support the sampler in an upright position on a supporting surface.

The open upper end of the sampler receptacle 216 is closed by a removable partition wall or cover 232 having a shallow cup-shaped body 233. The cover has an annular bottom wall 234 and a cylindrical side wall 236 projecting upwardly from the edge of the bottom wall. About the upper end of the cover side wall 236 is an outwardly directed annular flange 238. The cover 232 is removably positioned in the upper end of the receptacle 216 with the cover body 233 fitting closely but removably within the upper end of the receptacle and with the cover flange 238 resting on the upper receptacle flange 222 to vertically support the cover in the receptacle. The O-ring 224 provides a liquid seal between the cover and the upper end of the receptacle.

The interior space of the receptacle 216 between the cover 232 and the bottom wall 220 of the receptacle forms a liquid collection chamber 240. The cover and the upper side wall portion 212 of the receptacle form an upwardly opening liquid catch basin 242 above the collection chamber. The cover forms the floor of this basin. The upper receptacle side wall portion 212 forms the side wall of the basin which terminates at its upper end in the rim 214. The center of the cover wall 234 has a shallow coaxial circular recess 243 containing a relatively large coaxial circular opening 244 circumferentially surrounded by a depending flange 246.

Positioned on the cover 232 within the cover recess 243 and opening 244 are liquid inlet means 248 similar to the inlet means of the liquid sampling device in FIGS. 1–3. As shown best in FIG. 6, the inlet means 248 comprises an inlet fitting 250 including an upper float valve cage 252, a lower float valve cage 254, and a strainer 256 about the upper valve cage. The upper valve cage 252 includes a tube 258 having a multiplicity of flow openings in its wall and closed at its lower end by an integral coaxial circular wall or plate 260. This plate projects radially beyond the tube to form a coaxial circular flange about the lower end of the tube. Extending through the plate 260 coaxial with the tube 258 is an inlet passage 262 surrounded by a depending short cylindrical sleeve 264 depending from the plate. The lower end of this sleeve flares outwardly to form a downwardly facing lower valve seat 266 about the lower end of the passage 262. About the upper end of the passage 262 is an upwardly facing upper valve seat 268.

The lower valve cage 254 comprises a sleeve 270 having a multiplicity of flow openings in its wall and an annular flange 272 about its upper open end. Fixed within the lower end of the sleeve 270 is an internally threaded nut 274. The upper flange 272 of the lower cage 254 seats against and is rigidly joined to the underside of the upper cage plate 260 with the two cage sleeves 258, 270 coaxially aligned.

The strainer 256 of the inlet fitting 250 has an inverted cup shape. The lower edge of the strainer is rigidly joined to the outer edge of the upper valve cage plate 260, as by crimping the strainer edge over the plate edge, as shown. Fixed in the upper end of the strainer is a disc 276 which fits within the upper end of the upper cage sleeve 258.

Freely movable within the upper and lower valve cages 252, 254 are ball float valves 278, 280, respectively, which form, with the upper and lower valve seats 268, 266, upper and lower inlet valve means 282, 284. The upper float valve 278 is movable downwardly to its closed position of FIGS. 5 and 6 against the upper valve seat 268 to close the inlet passage 262. The upper float valve is movable upwardly away from the upper valve seat to an open position against an adjustable limit stop 286 to open the inlet passage. The limit stop 286 is threaded in the strainer disc 276 for adjustment toward and away from the upper valve seat 268 to adjust the maximum open flow area of the upper valve means 282. The lower float valve 280 is movable downwardly to its open position of FIGS. 5 and 6 away from the lower valve seat 266 to open the inlet passage 262, and upwardly to its closed position against the lower valve seat to close the inlet passage.

Figures 11, 12, 13, 14:
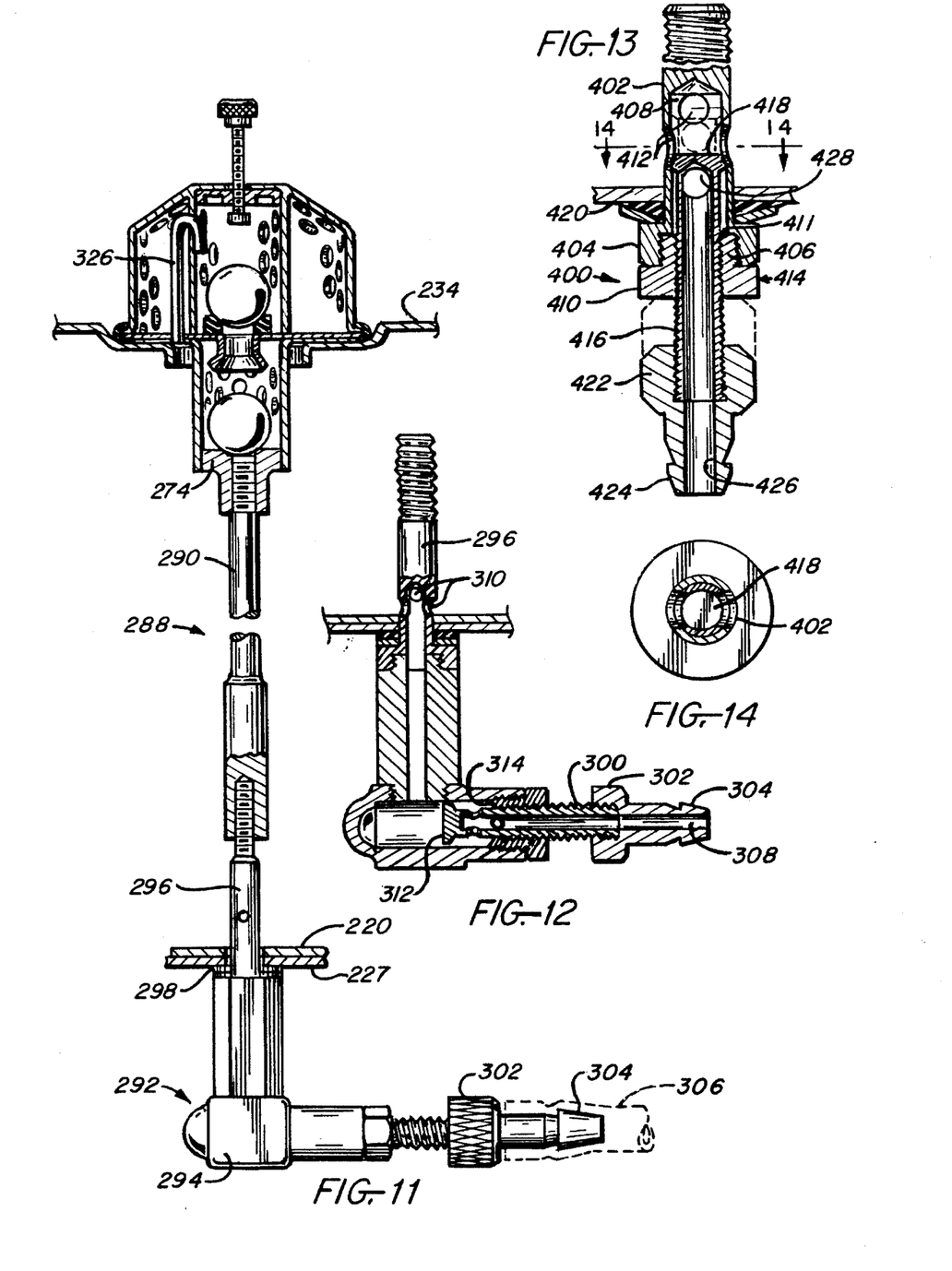
FIG. 11 is an enlarged fragmentary view of the liquid sampling device of FIG. 5.
FIG. 12 is a further enlarged axial section through a collection chamber drain valve shown in FIG. 11.
FIG. 13 is a longitudinal section through a modified drain valve.
FIG. 14 is a section taken on line 14—14 in FIG. 13.

The sampler receptacle 216, cover 232, and inlet means 248 are releasably joined in assembled relation by connecting means 288. As best shown in FIG. 11, this connecting means comprises a rod 290 threaded at its upper end in the nut 274 of the lower valve cage 254. The lower end of the rod 290 is enlarged and defines a threaded axial socket for connection to a drain valve 292 located within the sampler base 226. Drain valve 292 has an L-shaped body 294, one arm of which (the vertical arm in FIG. 12) is threadedly joined to a threaded stem 296. This stem extends axially upward through the bottom wall 220 of the receptacle 216 and the top wall 227 of the base 226 and is threaded in the lower end of the connecting rod 290. About the base of the stem 296 is a shoulder supporting a seal ring 298 engaging the upper base wall 227.

The drain valve 292 is rotatable in one direction about the axis of the connecting rod 290 to tighten the connecting means 288 for firmly securing the sampler receptacle, cover, and inlet means in assembled, mutually sealed relation. The drain vale is rotatable in the opposite direction to release the connecting means 288 for disassembly of the sampler for cleaning, as illustrated in FIG 7. Fixed to the cover 232 are handles 299 for holding the sampler and placing the sampler in and removing it from the casing 206.

Threaded in the remaining horizontal arm of the drain valve body 294 is a drain tube 300 having an external knurled portion 302 by which the tube may be rotated. On the outer end of the drain tube is a hose nipple 304 for connection to a drain hose 306 extending through the base sidewall opening 228. The drain valve contains a passage 308 which extends at one end through the vertical arm of the valve body 294 and the threaded stem 296, and opens into the sampler collection chamber 24 through ports 310 in the stem. The other end of the valve passage 308 extends axially through the horizontal arm of the valve body 294, the drain tube 300 and the hose nipple 304. On the inner end of the drain tube 300 is a valve head 312. This valve head is movable axially into and from engagement with a valve seat 314 about the valve passage 308 by rotation of the drain tube to open and close the passage.

Figure 9:
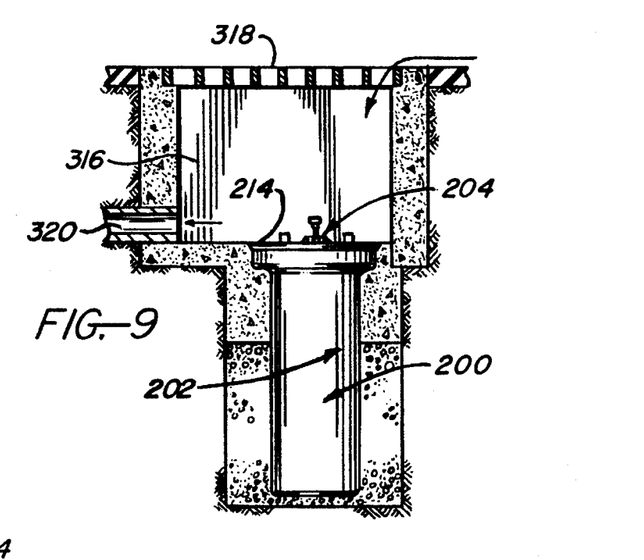
FIG. 9 and 10 illustrate two alternative sump arrangements for locating the sampling device of FIGS. 5–8 in sampling position.
Figure 10:
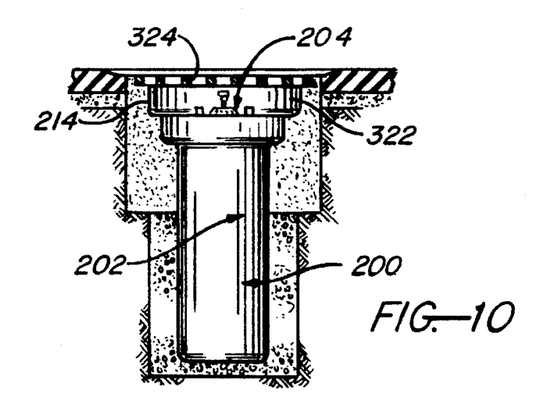

FIGS. 9 and 10 illustrate two different ways of locating the sampling device 200 in sampling position for the storm water sampling or leak sampling applications mentioned earlier. In FIG. 9, the sampler casing 202 of the sampling device is embedded in concrete at the bottom of a relatively deep sump 316 with the lip 214 of the casing flush with the bottom of the sump. The sump is covered by a grate 318 flush with ground level and has a drain line 320 leading from the bottom of the sump. In FIG. 10, the casing 202 is embedded in concrete with the upper casing lip 214 flush with the bottom of a shallow cavity 322 covered by a grate 324 flush with ground level.

The sampling device 200 is used in essentially the same way as the sampling device 10 of FIGS. 1–3 except for the following differences. In FIGS. 1–3, the upper float valve seat 78 is located at upper end of the inlet riser 52. When the liquid level in the basin 40 rises above the level of the upper valve seat, the upper float valve is raised from the seat to permit liquid flow into the inlet riser and then through the riser into the collection chamber 20. In the sampling device 200, the lowest flow openings in the side wall of the upper valve cage 258 are located a distance above the floor 234 of the basin 242, and the solid lower portion of the cage below these lowest openings forms an inlet riser 325. The upper valve seat 268 is located at the bottom of this inlet riser. Accordingly, when the liquid level in the basin 242 reaches the upper end of the inlet riser 325, the liquid flows over and to the bottom of the riser and then raises the upper float valve 278 from the upper valve seat 268 to permit flow into the collection chamber. The inlet riser serves the same purposes a the inlet riser in the sampling device 10.

The maximum flow opening of the upper float valve means 282 is adjustable by adjustment of the limit stop 286.

This upper valve adjustment adjusts the maximum liquid flow rate from the basin 242 into the collection chamber 240 and thereby the overall sampling duration of the sampling device. As a consequence, the limit stop adjustment permits use of the sampling device 200 for time composite storm water sampling. The inlet means 248 of the sampling device 200 also has a vent tube 326 which extends upwardly from the cover wall 234, laterally into the upper valve cage 258, and then downwardly toward the cover wall and contains a vent passage for venting air from the top of the collection chamber 240 to atmosphere during filling of the chamber with liquid.

After the desired liquid sample has been collect, the sampler 204 is removed for the casing 202 by its handles 299 and carried to a laboratory where the sample is drained from the sampler through the drain valve 292 for analysis. After each use, the sampler is disassembled and thoroughly cleaned. In this regard, it will be seen that removal of the cover 232 from the sampler receptacle 202 provides a large opening in the upper end of the receptacle through which the interior of the collection chamber 240 may be easily cleaned.

FIGS. 13 and 14 illustrate an in-line drain valve 400 for use on the liquid sampling device 200 in place of the right angle drain valve 292. The in-line valve includes an elongate drain bolt 402 having an upper threaded end for threaded connection with the lower end of the connecting rod 290 of the sapling device 200. The lower end of the drain bolt 402 is radially enlarged to form a coaxial shoulder portion 404. Axially entering the lower end of this shoulder portion is an internally threaded socket 406 which continues in a smaller diameter bore 408 extending axially upward through a lower end portion of the drain bolt. Threaded in the socket 406 is an internally threaded bushing 410 which forms a valve seat 411 about the lower end of the bore 408. The drain bolt 402 contains two axially spaced pairs of ports 412 opening to the bore along mutually perpendicular axes.

Threaded in the bushing 412 is a drain tube 414. This drain tube has a lower threaded portion, an upper valve head 418, and an intervening circumferential recess 420. The valve head 418 is slightly larger in diameter than the threaded bore in the bushing 412. Threaded on and rigidly fixed to the lower end of the drain tube is a knurled grip 422 from which a hose nipple 424 extends axially of the tube. Extending axially through the drain tube 414, the grip 422, and the nipple 424 is a passage 426 which opens radially into the upper drain tube recess 420 through ports 428 in the bottom of the recess.

The drain valve 400 is installed on the liquid sampling device 200, in place of the right angle drain valve 292, by inserting the drain bolt 402 through the bottom wall 220 of the device and threading the upper end of the bolt into the lower end of the connecting rod 290 to firmly join the sampler receptacle 216, cover 232, and inlet means 248 in the same manner as described earlier in connection with the sampling device 200.

The drain valve 400 is closed by rotating the grip 422 in a direction to move the tube downwardly until its valve head 418 engages the bushing valve seat 411. In this closed position, the drain tube ports 428 are situated below the valve seat 411 so that liquid cannot enter the drain valve passage 426 from the collection chamber 240. The drain valve is opened by rotating the drain tube in the opposite direction to move its valve head 418 upwardly from the valve seat 411 to a position in which the drain tube recess 420 opens radially outward to either the lower pair of drain bolt ports 412 only or to both pairs of these ports. Liquid flow can then occur from the sampler collection chamber 240 through the lower drain bolt ports 412 and the drain tube ports 428 into the drain valve passage 426. Operation of the liquid sampling device 200 with the drain valve 400 is the same as with drain valve 292.

It is evident at this point that the inlet valve means, i.e. the two valve balls together with their valve seat and cages, embodied in each described embodiment of the invention constitutes and inlet float valve means which closes the liquid inlet passage to the sample collection chamber except when both of the following conditions exist: (a) the inlet of the inlet passage is submerged in the liquid being sampled, and (b) the sample collection chamber contains less than a predetermined liquid volume. This inlet float valve means has an open mode in which the inlet valve opens the inlet passage to permit liquid flow into the collection chamber and a closed mode in which the inlet valve closes the inlet passage to seal the chamber and is operable to each of these modes by forces including a buoyant force produced by the liquid being sampled, i.e. by gravitational and buoyant forces.

I claim:

1. A liquid sampling device comprising:

a receptacle including a sample collection chamber having normally upper and lower ends, liquid inlet means at the upper end of said chamber including an inlet passage to said collection chamber having a normally upper inlet through which liquid to be sampled may enter said chamber when liquid covers said passage inlet, and means whereby a collected sample may be removed from said chamber, and wherein said sampling device is adapted to be placed in a sampling position wherein said inlet is disposed to receive liquid to be sampled, and said inlet means includes float valve means responsive to submergence of said inlet in liquid for closing said passage except when said inlet is submerged in liquid, thereby to block entry of foreign matter into said collection chamber when said inlet is not submerged in liquid.

2. A liquid sampling device according to claim 1 including:

a normally upwardly opening basin at the upper end of said receptacle for receiving the liquid to be sampled and having a lower floor and an upper rim above said floor, and wherein said inlet is located at an inlet level between said basin floor and rim, whereby liquid filling said basin at least to said inlet level can flow from said basin through said inlet and passage into said collection chamber, and said valve means is responsive to the liquid level in said basin and opens when liquid fills said basin at least to said inlet level and closes when the level of liquid, if any, in the basin is below said said inlet level.

3. A liquid sampling device comprising:

a receptacle including a sample collection chamber having normally upper and lower ends, liquid inlet means at the upper end of said chamber including an inlet passage to said collection chamber having a normally upper inlet through which liquid to be sampled may enter said chamber when the liquid covers said passage inlet, and means whereby a collected sample may be removed from said chamber, and wherein said sampling device is adapted to be placed in a sampling position wherein said inlet of said inlet passage is disposed to receive liquid to be sampled to provide a liquid sample in said chamber, said sample collection chamber is adapted to contain a liquid sample of predetermined volume, said inlet means includes inlet float valve means which close said inlet passage except when both of the following conditions exist: (a) said inlet of said inlet passage is submerged in liquid, and (b) said collection chamber contains less than said predetermined volume of liquid, and said inlet float valve means has an open mode in which said float valve means opens the inlet passage to permit liquid flow into the collection chamber and a closed mode in which said float valve means closes the inlet passage to seal the chamber, and said float valve means is operable to each of said modes by forces including a buoyant force produced by the liquid being sampled.

4. A liquid sampling device comprising:

a receptacle including a sample collection chamber having normally upper and lower ends, liquid inlet means at the upper end of said chamber including an inlet passage to said collection chamber having a normally upper inlet through which liquid to be sampled may enter said chamber when the liquid covers said passage inlet, and wherein said sampling device is adapted to be placed in a sampling position wherein said inlet of said inlet passage is disposed to receive liquid to be sampled to provide a liquid sample in said chamber, said sample collection chamber is adapted to contain a predetermined volume of liquid, said inlet means includes inlet float valve means having a standby mode in which said float valve means close said inlet passage against entry of foreign matter into said collection chamber, a sampling mode in which said float valve means open said inlet passage for entry of liquid being sampled into said collection chamber, and a sample containment mode in which said float valve means close said inlet passage against entry of material into and loss of material from said collection chamber, said inlet valve means assume said standby mode in the absence of liquid covering said said inlet end of said inlet passage, said sampling mode when said inlet end of said inlet passage is covered with liquid and said collection chamber contains less than said predetermined volume of liquid, and said sample containment mode when said collection chamber contains aid predetermined volume of liquid, and said float valve means is operable to each of said modes by forces including a buoyant force produced by the liquid being sampled.

5. A liquid sampling device comprising:

a receptacle including a sample collection chamber having normally upper and lower ends, liquid inlet mean at the upper end of said chamber including an inlet passage to said collection chamber having a normally upper inlet through which liquid to be sampled may enter said chamber when the liquid covers said passage inlet, and mean whereby a collected sample may be removed from said chamber, and wherein said sampling device is adapted to be placed in a sampling position wherein said inlet of said inlet passage is disposed to receive liquid to be sampled to provide a liquid sample in said chamber, said inlet means includes at least the first valve means of the following first and second valve means: first valve means for closing said inlet passage except when said inlet of said inlet passage is covered with liquid, and second valve mean for closing said inlet passage when said collection chamber contains a predetermined volume of liquid, said first valve means comprises an upper normally upwardly facing valve seat about said inlet of said inlet passage, and an upper float valve movable downwardly into contact with said seat to close said inlet of said inlet passage in the absence of liquid covering said inlet of said inlet passage and movable upwardly away from said valve seat by liquid covering said inlet of said inlet passage to open said inlet, and said second valve means comprises a lower normally downwardly facing valve seat about the lower end of said inlet passage, and a lower float valve movable upwardly into contact with said lower valve seat by liquid filling said collection chamber to a predetermined level to close the lower end of said inlet passage and movable downwardly away from said lower valve seat to open the lower end of said inlet passage when the liquid level in said collection chamber is below said predetermined level.

6. A liquid sampling device according to claim 5 in combination with means for conducting liquid to be sampled to said sampling device, and wherein said inlet means is disposed to receive liquid from said liquid conducting means.

7. A liquid sampling device according to claim 5 in combination with a surface for conducting liquid to be sampled to said sampling device, and wherein said device is disposed in a sump opening upwardly through said surface with said inlet means located to receive liquid entering the sump.

8. A liquid sampling device comprising:

a receptacle including a sample collection chamber having normally upper and lower ends, liquid inlet means at the upper end of said chamber including an inlet passage to said collection chamber having a normally upper inlet through which liquid to be sampled may enter said chamber when the liquid covers said passage inlet, and means whereby a collected sample may be removed from said chamber, and wherein said sampling device is adapted to be placed in a sampling position wherein said inlet of said inlet passage is disposed to receive liquid to be sampled to provide a liquid sample in said chamber, said inlet means includes float valve means comprising a valve seat about said inlet passage, a float valve member movable into and from contact with said valve seat to control flow through said passage, and manually adjustable means for adjusting the maximum separation of said valve member from said valve seat to adjust the maximum liquid inflow rate into said collection chamber.

9. A liquid sampling device comprising:

a receptacle including a sample collection chamber having normally upper and lower ends, liquid inlet means at the upper end of said chamber including an inlet passage to said collection chamber having a normally upper inlet through which liquid to be sampled may enter said chamber when the liquid covers said passage inlet, and wherein said sampling device is adapted to be placed in a sampling position wherein said inlet of said inlet passage is disposed to receive liquid to be sampled to provide a liquid sample in said chamber, said sample collection chamber is adapted to contain a predetermined volume of liquid, said inlet means includes inlet valve means having a standby mode in which said inlet valve mean close said inlet passage against entry of foreign matter into said collection chamber, a sampling mode in which said inlet valve means open said inlet passage for entry of liquid being sampled into said collection chamber, and a sample containment mode in which said inlet valve mean close said inlet passage against entry of material into and loss of material from said collection chamber, said inlet valve means assume said standby mode in the absence of liquid covering said said inlet end of said inlet passage, said sampling mode when said inlet end of said inlet passage is covered with liquid and said collection chamber contains less than said predetermined volume of liquid, and said sample containment mode when said collection chamber contains said predetermined volume of liquid, and said inlet valve means includes adjustable means for adjusting the maximum liquid inflow rate into said collection chamber in said sampling mode.

10. A liquid sampling device comprising:

a receptacle including a sample collection chamber having normally upper and lower ends, liquid inlet means at the upper end of said chamber including an inlet passage to said collection chamber having a normally upper inlet through which liquid to be sampled may enter said chamber when the liquid covers said passage inlet, and means whereby a collection sample may be removed from said chamber, and wherein said sampling device is adapted to be placed in a sampling position wherein said inlet of said inlet passage is disposed to receive liquid to be sampled to provide a liquid sample in said chamber, said inlet means includes at least one of the following first and second valve mean: first valve mean for closing said inlet passage except when said inlet of said inlet passage is covered with liquid, and second valve mean for closing said inlet passage when said collection chamber contains a predetermined volume of liquid, said first valve means comprises an upper normally upwardly facing valve seat about said inlet of said inlet passage, and an upper float valve movable downwardly into contact with said seat to close said inlet of said inlet passage in the absence of liquid covering said inlet of said inlet passage and movable upwardly away from said valve seat by liquid covering said inlet of said inlet passage to open said inlet, said second valve means comprises a lower normally downwardly facing valve seat about the lower end of said inlet passage, and a lower float valve movable upwardly into contact with said lower valve seat by liquid filling said collection chamber to a predetermined level to close the lower end of said inlet passage and movable downwardly away from said lower valve seat to open the lower end of said inlet passage when the liquid level in said collection chamber is below said predetermined level, and said first valve means includes adjustable limit stop means for adjusting the maximum separation of said upper float valve from said upper valve seat.

11. A liquid sampling device comprising:

a receptacle including a sample collection chamber having normally upper and lower ends, liquid inlet means at the upper end of said chamber including an inlet passage to said collection chamber having a normally upper inlet through which liquid to be sampled may enter said chamber when the liquid covers said passage inlet, and means whereby a collected sample may be removed from said chamber, and wherein said sampling device is adapted to be placed in a sampling position wherein said inlet of said inlet passage is disposed to receive liquid to be sampled to provide a liquid sample in said chamber, said receptacle includes a lower body having a lower end wall, and an upper end wall closing an upper end of said body, said body and said upper end wall form said collection chamber, and said upper end wall contains an opening to said collection chamber, said inlet means comprises an inlet fitting including float valve means for controlling flow through said inlet passage, at least one of said upper end wall and inlet fitting is separable from said receptacle body to permit cleaning of said collection chamber, and said sampling device includes connecting means releasably securing said fitting, upper end wall, and receptacle body in assembled relation.

12. A liquid sampling device according to claim 11 wherein:

said connecting means comprises a connecting rod secured to said inlet fitting and extending downwardly from said fitting through said collection chamber to said lower end wall, and means secured to a lower end of said rod and accessible at an under side of said lower end wall for securing and releasing said connecting means.

13. A liquid sampling device according to claim 12 wherein:

said means secured to said lower end of said connecting rod comprises a grip, and said rod is threaded in one of said fitting and grip, and said grip is rotatable to release and secure said connecting means.

14. A liquid sampling device according to claim 12 wherein:

said means whereby a collected sample may be removed from said collection chamber comprises a drain valve, said drain valve comprises said means secured to said lower end of said connecting rod, said rod is threadedly joined to one of said inlet fitting and drain valve, and said drain valve is rotatable to release and secure said connecting means, and said drain valve has a drain passage opening to the bottom of said collection chamber and includes valve means for opening and closing said drain passage.

15. A liquid sampling device according to claim 11 wherein:

said upper end wall is permanently joined to said receptacle body, and said inlet fitting is removable from said upper end wall by release of said connecting means to permit cleaning of said collection chamber through the opening in said upper end wall.

16. A liquid sampling device according to claim 11 wherein:

said receptacle body has an open upper end, said upper end wall comprises a removable cover closing said open end of said body, and said cover is removable from said body by release of said connecting means to permit cleaning of said collection chamber through the open upper end of said body.

17. A liquid sampling device comprising:

a receptacle having normally upper and lower ends and a sample collection chamber between said ends, an upwardly opening basin at the upper end of said receptacle for receiving a liquid to be sampled and having an upper rim and a floor, inlet means at the upper end of said receptacle including an inlet passage extending through said basin floor to said collection chamber and having a normally upper inlet opening to said basin below said basin, rim, whereby liquid to be sampled may flow from said basin, through said inlet passage, into said collection chamber chamber when the liquid in said basin covers said passage inlet, means whereby liquid may be removed from said chamber, and wherein said sampling device is adapted to be placed in a sampling position wherein said basin is disposed to receive liquid to be sampled, and said inlet means includes float valve means responsive to the liquid level in said basin for closing said passage inlet end except when said basin contains sufficient liquid to cover said inlet end.

18. A liquid sampling device according to claim 17, wherein:

said inlet end of said inlet passage is located a distance above said basin floor.

19. A liquid sampling device comprising:

a receptacle having normally upper and lower ends and a sample collection chamber between said ends, an upwardly opening basin at the upper end of said receptacle for receiving a liquid to be sampled and having an upper rim and a floor, inlet means at the upper end of said receptacle including an inlet passage extending through said basin floor to said collection chamber and having a normally upper inlet opening to said basin below said basin rim, whereby liquid to be sampled may flow from said basin, through said inlet passage, into said collection chamber when the liquid in said basin covers said passage inlet, means whereby liquid may be removed from said chamber, and wherein said sampling device is adapted to be placed in a sampling position wherein said basin is disposed to receive liquid to be sampled, said sample collection chamber is adapted to contain a liquid sample of predetermined volume, and said inlet means includes inlet float valve means which close said inlet passage except when both of the following conditions exist: (a) liquid covers said inlet, and (b) said collection chamber contains less than said predetermined volume of liquid.

20. A liquid sampling device comprising:

a receptacle having normally upper and lower ends and a sample collection chamber between said ends, an upwardly opening basin at the upper end of said receptacle for receiving a liquid to be sampled and having an upper rim and a floor, inlet means at the upper end of said receptacle including an inlet passage extending through said basin floor to said collection chamber and having a normally upper inlet opening to said basin below said basin rim, whereby liquid to be sampled may flow from said basin, through said inlet passage, into said collection chamber when the liquid in said basin covers said passage inlet, means whereby liquid may be removed from said chamber, and wherein said sampling device is adapted to be placed in a sampling position wherein said basin is disposed to receive liquid to be sampled, said sample collection chamber is adapted to contain a liquid sample of predetermined volume, said inlet means includes inlet float valve means having a standby mode in which the inlet valve means close said inlet passage against entry of foreign matter into said collection chamber, a sampling mode in which the inlet valve means open said inlet passage for entry of liquid being sampled into said collection chamber, and a sample containment mode in which the inlet valve means close said inlet passage against entry of material into and escape of material from said collection chamber, and the inlet valve means assumes said standby mode in the absence of liquid covering said inlet end of said inlet passage, said sampling mode when said inlet end of said inlet passage is covered with liquid and said collection chamber contains less than said predetermined volume of liquid, and said sample containment mode when said collection chamber contains at least said predetermined volume of liquid.

21. A liquid sampling device comprising:

a receptacle having normally upper and lower ends and a sample collection chamber between said ends, an upwardly opening basin at the upper end of said receptacle for receiving a liquid to be sampled and having an upper rim and a floor, inlet means at the upper end of said receptacle including an inlet passage extending through said basin floor to said collection chamber and having a normally upper inlet opening to said basin below said basin rim, whereby liquid to be sampled may flow from said basin, through said inlet passage, into said collection chamber when the liquid in said basin covers said passage inlet, means whereby liquid may be removed from said chamber, and wherein said sampling device is adapted to be placed in a sampling position wherein said basin is disposed to receive liquid to be sampled, and said inlet means includes at least one of the following first and second float valve means: first valve means for closing said inlet passage except when liquid in said basin covers said inlet of said inlet passage, and second valve means for closing said inlet passage when said collection chamber contains at least a predetermined volume of liquid.

22. A liquid sampling device according to claim 21, wherein:

said first valve means comprises an upper normally upwardly facing valve seat about said inlet end of said inlet passage, an upper float valve movable downwardly into contact with said seat to close the upper end of said inlet passage when the liquid level in said basin is below the inlet end of said inlet passage and movable upwardly away from said valve seat to open the upper end of said inlet passage by liquid filling said basin to a level above the inlet end of said inlet passage, and a cage containing said float valve, and said second valve means comprises a lower normally downwardly facing valve seat about the lower end of said inlet passage, a lower float valve movable upwardly into contact with said lower valve seat by liquid filling said collection chamber at least to a predetermined level to close the lower end of said inlet passage and movable downwardly away from said lower valve seat to open the lower end of said inlet passage when the liquid level in said collection chamber is below said predetermined level, and a cage containing said lower float valve.

23. A liquid sampling device according to claim 11 wherein:

said first valve means includes adjustable limit stop means for adjusting the maximum separation of said upper float valve from said upper valve seat.

24. A liquid sampling device according to claim 21 in combination with means for conducting liquid to be sampled to said sampling device, and wherein said basin is disposed to receive liquid from said liquid conducting means.

25. A liquid sampling device according to claim 21 in combination with means for conducting liquid to be sampled to said sampling device, and wherein said device is disposed in a sump opening upwardly through said surface with said basin located to receive liquid entering the sump.

26. A liquid sampling device according to claim 25, wherein:

said device is a storm water sampler, and said surface is a ground surface of an industrial property.

27. The subject matter of claim 25 including:

a casing embedded in the bottom of said sump having an open upper end opening to said sump and removably receiving said receptacle with said basin and inlet means located at said casing upper end.

28. The subject matter of claim 21 wherein said sampling device includes:

a portable relatively thin-walled casing having an open upper end removably receiving said receptacle, and means vertically supporting said receptacle in said casing with said inlet means at the upper end of said casing.

29. The subject matter of claim 28, wherein:

said means vertically supporting said receptacle in said casing comprises an upwardly facing circumferential shoulder within said casing, and a circumferential flange about the upper end of said receptical resting on said shoulder, and said casing has a side wall portion extending above shoulder and forming said basin with said basin floor.

30. A liquid sampling device comprising:

a receptacle having normally upper and lower ends and a sample collection chamber between said ends, an upwardly opening basin at the upper end of said receptacle for receiving a liquid to be sampled and having an upper rim and a floor, inlet means at the upper end of said receptacle including an inlet passage extending through said basin floor to said collection chamber and having a normally upper inlet opening to said basin below said basin rim, whereby liquid to be sampled may flow from said basin, through said inlet passage, into said collection chamber when the liquid in said basin covers said passage inlet, means whereby liquid may be removed from said chamber, and wherein said sampling device is adapted to be placed in a sampling position wherein said basin is disposed to receive liquid to be sampled, said receptacle includes a lower body having a lower end wall, and an upper end closed by said basin floor, said inlet means comprises an inlet fitting on said basin floor, said inlet fitting including float means for controlling flow through said passage, at least one of said basin floor and inlet fitting is separable from said receptacle body to permit cleaning of said collection chamber, and said sampling device includes connecting means releasably securing said fitting, basin floor, and receptacle body in assembled relation.

31. A liquid sampling device according to claim 30, wherein:

said connecting means joins said inlet fitting and said lower end wall and comprises a connecting rod secured to said inlet fitting and extending downwardly from said fitting through said collection chamber to said lower end wall, and means secured to a lower end of said rod and accessible at an under side of said lower end wall for securing and releasing said connecting means.

32. A liquid sampling device according to claim 11 wherein:

said means secured to said lower end of said connecting rod comprises a grip, and said rod is threaded in one of said fitting and grip, and said grip is rotatable to release and secure said connecting means.

33. A liquid sampling device according to claim 31, wherein:

said drain valve comprises said means secured to said lower end of said connecting rod, said rod is threadedly joined to one of said fitting and drain, and said drain valve is rotatable to release and secure said connecting means, and said drain valve has a drain passage opening to the bottom of said collection chamber and includes valve means for opening and closing said drain passage.

34. A liquid sampling device according to claim 30, wherein:

said basin floor is permanently joined to said receptacle body, and said body has a side wall portion which projects above said floor, said basin floor and said side wall portion from said basin, and said inlet fitting is removable from said basin floor by release of said connecting means to permit cleaning of said collection chamber through the opening in said floor.

35. A liquid sampling device according to claim 30, wherein:

said receptacle body has an open upper end, an inner upwardly facing annular shoulder within said body, and a side wall portion projecting above said shoulder, said basin floor comprises a removable cover seating on said shoulder and closing said open end of said body, said cover and said side wall portion form said basin, and said cover is removable from said body by release of said connecting means to permit cleaning of said collection chamber through the open upper end of said body.

36. In combination:

a liquid sampling device comparing a receptacle including a sample collection chamber having normally upper and lower ends, liquid inlet means at the upper end of said chamber including an inlet passage to said collection chamber having a normally upper inlet through which liquid to be sampled may enter said chamber when the liquid covers said passage inlet, and means, for draining a collected sample, from said chamber, a casing removably receiving said receptacle with said inlet means located at said casing upper end, a surface for conducting liquid to be sampled to said sampling device, a sump opening upwardly through said surface, and wherein said inlet means includes at least one of the following first and second valve means; first valve means for closing said inlet passage except when said inlet of said inlet passage is covered with liquid, and second valve means for closing said inlet passage when said collection chamber contains a predetermined volume of liquid, and said casing is embedded in the bottom of said sump and removably contains said receptacle with said inlet means located to receive liquid entering the sump.

37. A liquid sampling device comprising:

a receptacle having normally upper and lower ends and a sample collection chamber between said ends, an upwardly opening basin at the upper end of said receptacle for receiving a liquid to be sampled and having an upper rim and a floor, inlet means at the upper end of said receptacle including an inlet passage extending through said basin floor to said collection chamber and having a normally upper inlet opening to said basin between said basin floor and said basin rim, whereby liquid to be sampled may flow from said basin, through said inlet passage, into said collection chamber when the liquid in said basin covers said passage inlet, means whereby liquid may be removed from said chamber, and wherein said sampling device is adapted to be placed in a normal sampling position wherein said basin is disposed to receive liquid to be sampled, and said chamber is sealed against leakage of liquid from the chamber when said sampling device occupies said normal sampling position.

38. A liquid sampling device comprising: an outer casing having a normally lower closed end and a normally upper open end, an outwardly directed annular flange about said open end, and an upstanding annular wall about the outer perimeter of said flange, a liquid sampler including a lower receptacle having a normally lower closed end and a normally upper open end, a cover extending across and beyond the open end of said receptacle to form an outwardly directed annular flange about the open end of the receptacle, and means joining said receptacle and cover, and wherein said liquid sampler is removably positioned within said casing with said sampler flange seating on said casing flange, and said sampling device includes an upwardly open basin above said liquid sampler, and a passage having an upper inlet opening to said basin and a lower end opening to the interior of said receptacle.

39. A liquid sampling device according to claim 38 including at least one of the following first and second valve means:

(a) first valve means for closing said passage except when said inlet passage inlet is covered with liquid, (b) second valve means for closing said passage when said collection chamber contains a predetermined volume of liquid.

40. A liquid sampling device comprising:

a receptacle having normally upper and lower ends and a sample collection chamber between said ends, a normally upwardly opening basin above said chamber having a normally lower floor and a normally upper rim and communicating with said collection chamber through a passage having a normally upper inlet opening to said basin below said basin rim and a normally lower end opening to said chamber, and at least the first valve means of the following first and second valve means for controlling flow through said passage; (a) first valve means including a first perforate cage within said basin, a first float valve member within said cage, and a first valve seat about said inlet engageably by said float valve member for closing said passage except when said inlet inlet is covered with liquid, (b) second valve means including a second perforate cage within said chamber, a second float valve member within said second cage, and a second valve seat about said lower passage end engagable by said second float valve member for closing said passage when said collection chamber contains a predetermined volume of liquid.

41. A storm water sampler comprising:

a receptacle including a normally lower storm water sample collection chamber, means for removing a collected storm water sample from said chamber, a normally upper and upwardly opening storm water receiving basin including a floor and a side wall rising above said floor having an upper rim, and a riser extending upwardly from said floor and containing a passage having a lower end opening to said sample collection chamber and an upper end opening to said basin at a level between said basin floor and said basin rim, and wherein said sampler is adapted to be placed in an anticipated flow path of storm water discharge from a property in such a way that storm water flows into and overflows said basin and enters said sample collection chamber through said passage to provide a storm water sample in said chamber, whereby a storm water sample from the first storm event of a storm season may be collected by placing the sampler in position prior to the first storm event.

42. A storm water sampler according to claim 41, including:

valve means in said passage for permitting storm water inflow through said passage into said chamber and blocking water outflow through said passage from said chamber.

43. A storm water sampler according to claim 41, including:

valve means in said passage for permitting storm water inflow through said passage into said chamber and blocking outflow of volatiles from said chamber through said passage.

44. A storm water sampler according to claim 41, including:
- valve means in said passage for permitting storm water inflow through said passage into said chamber and blocking water outflow through said passage from said chamber, and
- valve means in said passage for permitting storm water inflow through said passage into said chamber and blocking outflow of volatiles from said chamber through said passage.

45. A storm water sampler according to claim 41, including:
- valve means including a float ball in said passage for permitting storm water inflow through said passage into said chamber and blocking water outflow through said passage from said chamber, and
- valve means including a float ball in said passage for permitting storm water inflow through said passage into said chamber and blocking outflow of volaetiles from said chamber through said passage.

46. A storm water sampler according to claim 41, including:
- a receptacle including (a) a generally cup-shaped body having a normally lower end closed by a lower end wall, an opposite normally upper open end, and a rim circumferentially surrounding said open end, (b) a partition wall having a central opening and extending across the interior of said body between its ends and forming with said body a normally lower storm water sample collection chamber between said partition wall and said lower end wall and a normally upper storm water receiving basin having an open upper end circumferentially surrounded by said rim and a floor formed by said partition wall, (c) means for draining a collected storm water sample from said collection chamber, (d) a stormwater inlet fitting removably positioned within said partition wall opening and sealed to said partition wall about said partition wall opening and including an upstanding riser containing a passage having an upper end opening to said basin between said partition wall and said body rim and a lower end opening to said sample collection chamber, and (e) means releasably securing said fitting to said partition wall in fluid sealing relation to said partition wall about said partition wall opening, and wherein
- said sampler is adapted to be placed in an anticipated flow path of storm water discharge from a property in such a way that storm water flows into and overflows said basin and enters said sample collection chamber through said passage to provide a storm water sample in said chamber, whereby a storm water sample from the first storm event of a storm season may be collected by placing the sampler in position prior to the first storm event.

47. A storm water sampler according to claim 46, wherein:
- said fitting comprises valve means including a ball valve cage at the lower end of said riser into which the lower end of said passage opens and through when storm water flows from said passage into said collection chamber, a valve seat about said passage, and a buoyant valve ball within said cage which is separable from said valve seat to permit storm water inflow through said passage into said chamber and engageable with said valve seat to block water outflow through said passage from said chamber.

48. A storm water sampler according to claim 46, wherein:
- said fitting includes valve means including a ball valve cage at the upper end of said riser, a valve seat about the upper end of said passage, and a valve ball within said cage which is separable from said valve seat to permit storm water inflow through said passage into said chamber and engageable with said valve seat to block outflow of volatiles from said chamber through said passage.

49. A storm water sampler according to claim 46, wherein:
- said fitting includes (a) first valve means including a ball valve cage at the lower end of said riser into which the lower end of said passage opens and through which storm water flows from said passage into said collection chamber, a valve seat about said passage, and a buoyant valve ball within said cage which is separable from said valve seat to permit storm water inflow through said passage into said chamber and engageable with said valve seat to block water outflow through said passage from said chamber, and (b) second valve means including a second ball valve cage at the upper end of said riser, a second valve seat about the upper end of said passage, and a valve ball within said second cage which is separable from said second valve seat to permit storm water inflow through said passage into said chamber and engageable with said second valve seat to block outflow of volatiles from said chamber through said passage.

50. A storm water sampler according to claim 46, wherein:
- said means securing said fitting to said partition wall comprises a shaft extending downwardly from said fitting through said bottom wall, and a nut threaded on said shaft.

51. A storm water sampler according to claim 49, wherein:
- said means securing said fitting to said partition wall comprises a shaft extending downwardly from said fitting through said bottom wall, and a nut threaded on said shaft.

* * * * *